(12) United States Patent
Zong

(10) Patent No.: US 10,089,856 B1
(45) Date of Patent: Oct. 2, 2018

(54) PATTERN RECOGNITION METHODS TO IDENTIFY COMPONENT FAULTS

(71) Applicant: MOTOROLA SOLUTIONS, INC., Chicago, IL (US)

(72) Inventor: Jimmy Sixuan Zong, Plantation, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/600,098

(22) Filed: May 19, 2017

(51) Int. Cl.
G01R 31/00 (2006.01)
G08B 25/01 (2006.01)
G06F 11/30 (2006.01)
G01R 31/28 (2006.01)
G01R 31/30 (2006.01)

(52) U.S. Cl.
CPC .......... *G08B 25/018* (2013.01); *G01R 31/28* (2013.01); *G06F 11/3003* (2013.01); *A61B 2560/0271* (2013.01); *A61B 2560/0276* (2013.01); *G01R 31/30* (2013.01)

(58) Field of Classification Search
CPC .................. G01R 29/0814; G01R 29/0878
USPC .................. 340/635, 657, 660, 661, 664
See application file for complete search history.

(56) References Cited

U.S. PATENT DOCUMENTS

| 5,014,327 | A | * | 5/1991 | Potter | G06F 17/30982 382/218 |
| 5,592,093 | A | | 1/1997 | Klingbiel | |
| 7,111,205 | B1 | * | 9/2006 | Jahn | H04L 41/0681 709/224 |
| 7,476,123 | B2 | | 1/2009 | Kobayashi et al. | |
| 2002/0113600 | A1 | | 8/2002 | Swank, II | |
| 2007/0271014 | A1 | * | 11/2007 | Breed | B60J 10/00 701/31.9 |
| 2012/0021708 | A1 | * | 1/2012 | Murji | H03G 3/3042 455/115.4 |

* cited by examiner

*Primary Examiner* — Kevin Kim
(74) *Attorney, Agent, or Firm* — Michael Best & Friedrich LLP

(57) ABSTRACT

A communication device including an electrical component, a sensor, and an electronic processor. The sensor is coupled to the electrical component and is configured to sense an electrical characteristic of the electrical component. The electronic processor is configured to receive, from the sensor, a series of measurements corresponding to the electrical characteristic and determine, from the series of measurements, a first electrical characteristic profile. The electronic processor is further configured to compare the first electrical characteristic profile to a predetermined electrical characteristic profile to generate a comparison and generate an indication of a possible loose connection based on the comparison.

23 Claims, 5 Drawing Sheets

PATTERN RECOGNITION METHODS TO IDENTIFY COMPONENT FAULTS

BACKGROUND OF THE INVENTION

Electronic devices, for example, portable two-way radios and other communication devices, often include interchangeable components, for example, antennas and batteries. These components attach to the communication devices using connectors. Complete connections and properly performing components are important to the efficient transfer of radio frequency signals and electric power in the communication devices. Incomplete connections or faults in the components may cause failures in the communication devices.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
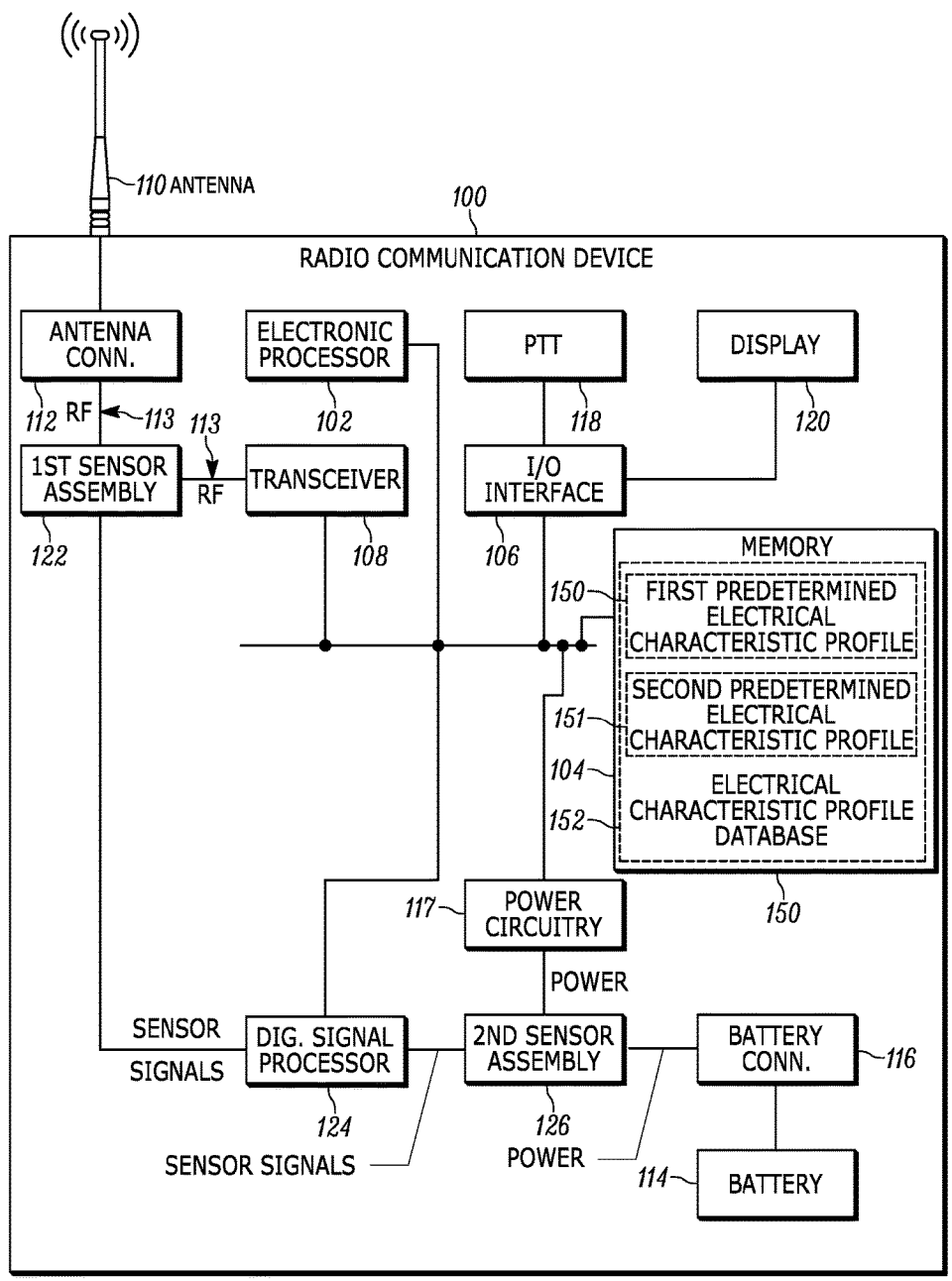
FIG. 1 is a diagram of a communication device in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The device and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

Component faults may cause device failures in the operation of communication and other electronic devices. Component faults include, for example, loose connections (for example, to a battery or an antenna), physical damage to a component, a misconfigured component (for example, a detuned antenna), an improperly or incompletely installed component, and the like. Such component faults are often difficult to diagnose and locate. Accordingly, methods and systems are provided herein to determine when there may be a component fault within a communication device.

One example embodiment provides a communication device. The communication device includes an electrical component, a sensor, and an electronic processor. The sensor is coupled to the electrical component and is configured to sense an electrical characteristic of the electrical component. The electronic processor is configured to receive, from the sensor, a series of measurements corresponding to the electrical characteristic and determine, from the series of measurements, a first electrical characteristic profile. The electronic processor is further configured to compare the first electrical characteristic profile to a predetermined electrical characteristic profile to generate a comparison and generate an indication of a possible component fault based on the comparison.

Another example embodiment provides a method for operating a communication device. The method includes receiving, from a sensor, a series of measurements corresponding to an electrical characteristic and determining, from the series of measurements, a first characteristic profile. The method further includes comparing the first electrical characteristic profile to a predetermined electrical characteristic profile to generate a comparison and generating an indication of a possible component fault based on the comparison.

Another example embodiment provides a portable radio communication device including an antenna, a transmitter coupled to the antenna via a transmission line, a sensor, and an electronic processor. The sensor is coupled to the transmission line and configured to sense an electrical characteristic of the transmission line. The electronic processor is connected to the sensor and configured to receive, from the sensor, a series of measurements corresponding to the electrical characteristic and determine, from the series of measurements, a first electrical characteristic profile. The electronic processor is further configured to compare the first electrical characteristic profile to a predetermined electrical characteristic profile to generate a comparison and generate an indication of a possible component fault based on the comparison.

For ease of description, some or all of the example systems presented herein are illustrated with a single exemplar of each of its component parts. Some examples may not describe or illustrate all components of the systems. Other example embodiments may include more or fewer of each of the illustrated components, may combine some components, or may include additional or alternative components.

FIG. 1 illustrates an example of a communication device 100. In some embodiments, the communication device 100 is a portable radio communication device. In the embodiment illustrated, the communication device 100 includes an electronic processor 102, a memory 104, an input/output interface 106, a transceiver 108, an antenna 110, an antenna connector 112, a battery 114, a battery connector 116, power circuitry 117, a push-to-talk (PTT) button 118, a display 120, a first sensor assembly 122, a digital signal processor 124, and a second sensor assembly 126. The illustrated components, along with other various modules and components are coupled to each other by or through one or more control, power, or data buses, that enable communication therebetween. The use of control and data buses for the interconnection between and exchange of information among the various modules and components would be apparent to a person skilled in the art in view of the description provided herein.

The electronic processor 102 obtains and provides information (for example, from the memory 104 and/or the input/output interface 106), and processes the information by, for example, executing one or more software instructions or modules, capable of being stored, in the memory 104 or another non-transitory computer readable medium (not shown). The software can include firmware, one or more applications, program data, filters, rules, one or more program modules, and other executable instructions.

The memory 104 can include random access memory (RAM), read only memory (ROM), or one or more other non-transitory computer-readable media, and may include a program storage area and a data storage area. The program storage area and the data storage area can include combinations of different types of memory, as described herein. In the embodiment illustrated, the memory 104 stores, among other things, one or more predetermined electrical characteristic profiles of the communication device 100 (described in detail below), for example a first predetermined electrical characteristic profile 150 and a second predetermined electrical characteristic profile 151. In some embodiments, one or more predetermined electrical characteristic profiles are stored in an electrical characteristic profile database 152. The electrical characteristic profile database 152 may be stored locally in the memory 104, or on a remote device (for example, a server).

In one embodiment, the electronic processor 102 is configured to retrieve from the memory 104 and execute, among other things, software related to control processes, for example, the methods described herein. For example, as described more particularly below with respect to FIG. 4, the electronic processor 102 makes use of the predetermined electrical characteristic profiles, for example the first predetermined electrical characteristic profile 150 and the second predetermined electrical characteristic profile 151 to determine whether faulty connections exist in or with respect to the antenna connector 112, the battery connector 116, or both.

The input/output interface 106 is configured to receive input and to provide output to peripherals. The input/output interface 106 obtains information and signals from, and provides information and signals to, (for example, over one or more wired and/or wireless connections) devices both internal and external to the communication device 100.

In the embodiment illustrated, the electronic processor 102 is configured to control the transceiver 108 to transmit and receive data to and from the communication device 100. The electronic processor 102 encodes and decodes digital data sent and received by the transceiver 108. The transceiver 108 transmits and receives radio signals to and from various wireless communications networks using the antenna 110. The electronic processor 102 and the transceiver 108 may include various digital and analog components, which for brevity are not described herein and which may be implemented in hardware, software, or a combination of both. In some embodiments, the digital signal processor 124 is integrated into the electronic processor 102. Some embodiments include separate transmitting and receiving components, for example, a transmitter and a receiver, instead of a combined transceiver 108.

The antenna 110 is communicatively coupled to the transceiver 108 via the antenna connector 112 and a transmission line 113. A first sensor assembly 122 is disposed between the antenna connector 112 and the transceiver 108. As described in more detail below with respect to FIG. 2, the first sensor assembly 122 senses radiofrequency (RF) signals sent between the transceiver 108 and the antenna 110, and outputs sensor signals relating to the RF signals to the digital signal processor 124.

The battery 114 provides power to the components of the communication device 100. Power from the battery 114 may be distributed by the power circuitry 117 and one or more power buses of the communication device 100 via the battery connector 116. A second sensor assembly 126 is disposed between the battery connector 116 and the power circuitry 117. As described in more detail below with respect to FIG. 3, the second sensor assembly 126 senses electrical power sent from the battery 114, and outputs sensor signals relating to the electrical power to the digital signal processor 124.

The push-to-talk button 118 may be used by a user of the communication device 100 to control push-to-talk communications. Pressing the push-to-talk button 118 activates the transceiver 108 and causes transmission of an audio communication from the communication device 100 to one or more other electronic communication devices. Push-to-talk communication may be between one individual and another individual or between one individual and a group of individuals (for example, via a talk group).

The display 120 is a suitable display, for example, a liquid crystal display (LCD) touch screen, or an organic light-emitting diode (OLED) touch screen. In some embodiments, the communication device 100 includes a graphical user interface (GUI) (for example, generated by the electronic processor 102, from instructions and data stored in the memory 104, and presented on the display 120), that enables a user to interact with the communication device 100. The graphical user interface presented herein allows interaction with the communication device 100 using gesture-based inputs. In other embodiments, gestures could be captured via a cursor-control device and through input actions such as mouse clicks. Thus, a touch screen is not necessary in all instances. In some embodiments, the communication device 100 does not include the display 120.

In some embodiments, the communication device 100 is a digital portable two-way radio. In other embodiments, the communication device 100 may be a smart telephone, a mobile computing device, a combination of the foregoing, or another portable or mobile electronic device containing software and hardware enabling it to operate as described herein.

Figure 2:
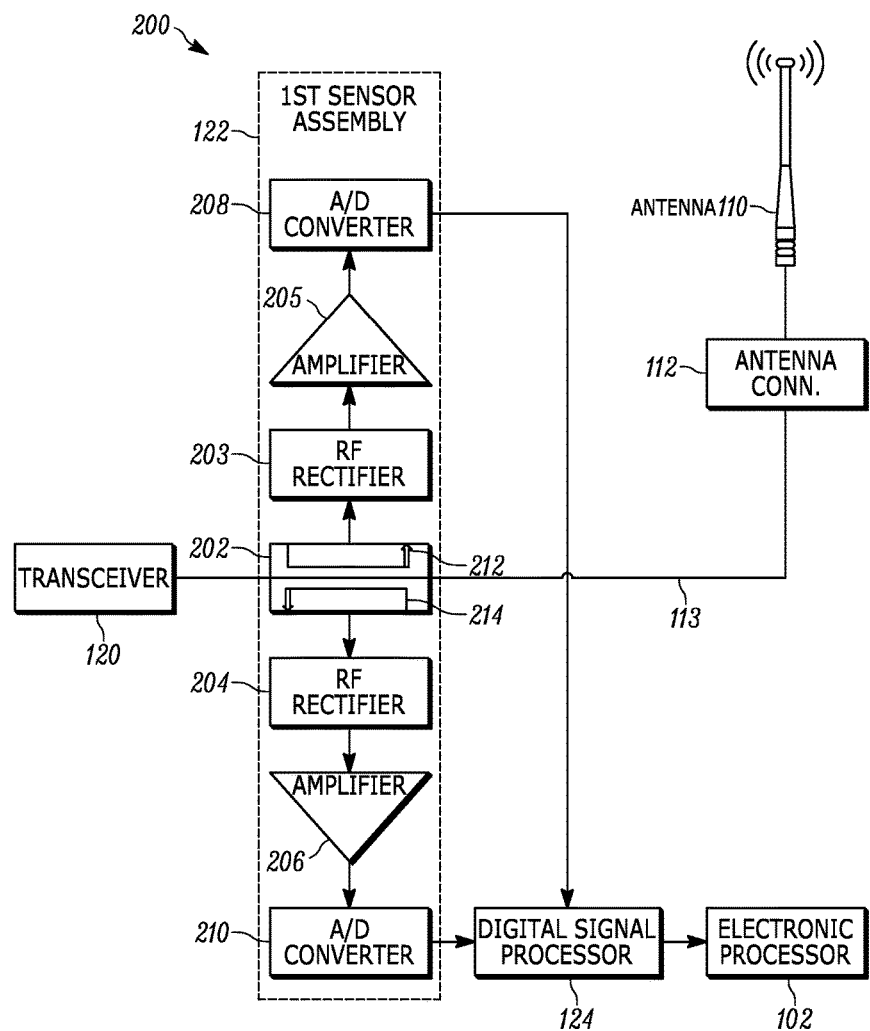
FIG. 2 is diagram of a sensor assembly at an antenna connector of the communication device of FIG. 1.

FIG. 2 illustrates a schematic diagram 200 of an example of the first sensor assembly 122. The first sensor assembly 122 includes a voltage standing wave ratio (VSWR) sensor 202, a first radio frequency rectifier 203, a second radio frequency rectifier 204, a first amplifier 205, a second amplifier 206, a first analog to digital (A/D) converter 208, and a second A/D converter 210. The VSWR sensor 202 includes a first directional coupler 212 and a second directional coupler 214 electromagnetically coupled to the communication line between the transceiver 108 and the antenna connector 112. The first directional coupler 212 detects the forward waves transmitted from the transceiver 108 through the antenna connector 112 to the antenna 110. The second directional coupler 214 detects reflected waves reflected back from the antenna 110. The RF rectifiers 203 and 204 each convert the forward and reflected signals, respectively, from a radio frequency signal to a DC signal. The forward and reflected signals are each amplified via the amplifiers 205 and 206 respectively and converted to digital signals via the A/D converters 208 and 210 respectively. The digital signals are transmitted to the digital signal processor 124 where the ratio of the detected signal levels is calculated to determine the reflection coefficient and VSWR. The digital signal processor 124 may transmit the signal information to the electronic processor 102 for further processing.

Figure 3:
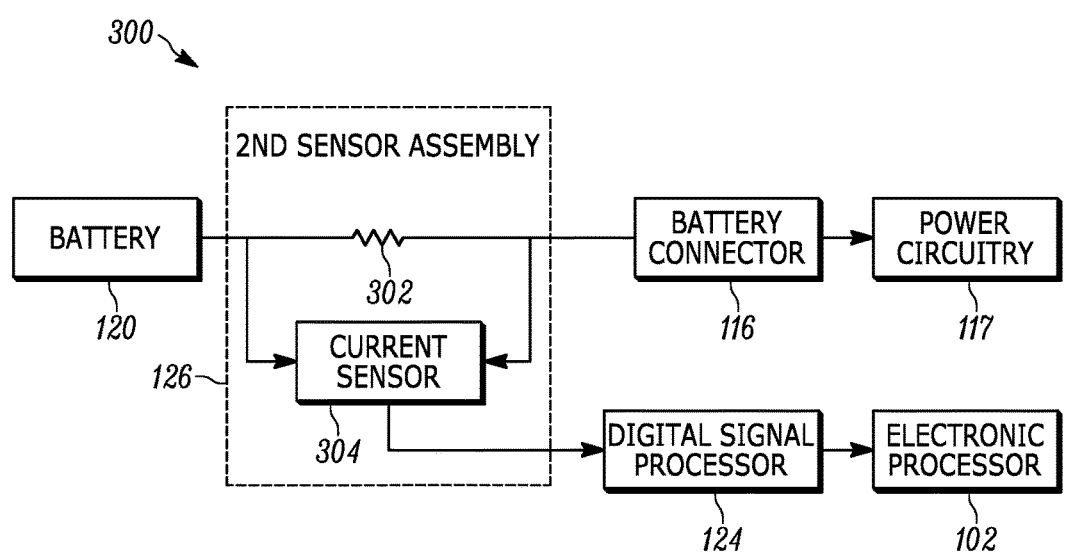
FIG. 3 is diagram of a sensor assembly at a battery connector of the communication device of FIG. 1.

FIG. 3 illustrates a diagram 300 of an example of the second sensor assembly 126. The second sensor assembly 126 includes a sense-resistor 302 in parallel with a current sensor 304. The current sensor 304 measures the current sourced by the battery 114 through the battery connector 116 to the power circuitry 117. The current sensor 304 does so by measuring the current through the sense-resistor 302 and transmits the signal to the digital signal processor 124 to process. In some embodiments, the second sensor assembly 126 is positioned to obtain the electrical characteristic by sampling the current from a power amplifier current sensor (not shown) of the power circuitry 117. The digital signal processor 124 may transmit the signal information to the electronic processor 102 for further processing.

Figure 4:
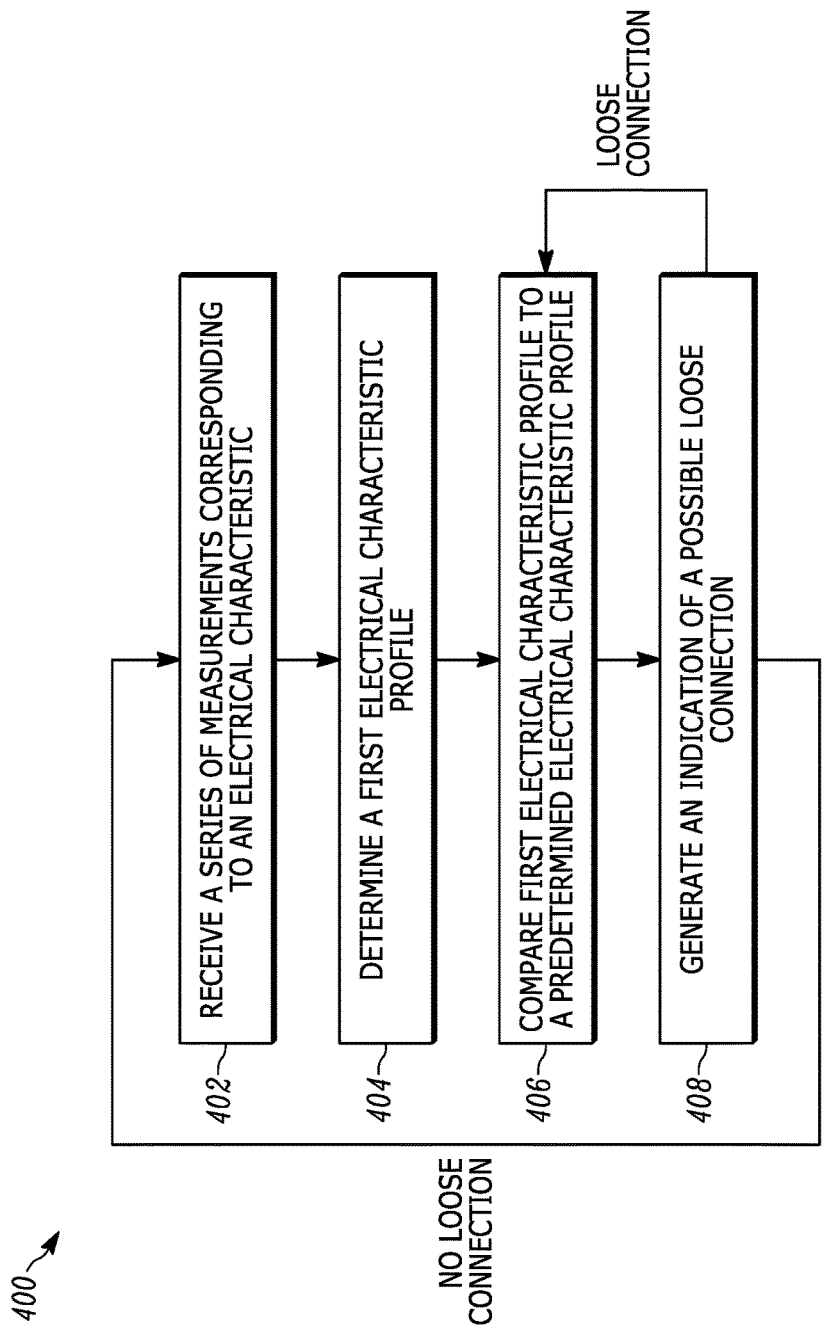
FIG. 4 is a flowchart illustrating the method for operating the communication device of FIG. 1.

FIG. 4 illustrates a flowchart of an example method 400 operating the communication device 100 for determining a possible component fault. As an example, the method 400 is explained in terms of a loose connection to either a battery or an antenna. In other embodiments, the method 400 may be used to determine other types of component faults, for example, a detuned antenna, a damaged battery, a faulty connector, an improperly installed component, a misconfigured component, and the like. The example method 400 is also described in terms of the first sensor assembly 122 and the second sensor assembly 126 as illustrated in FIGS. 2 and 3 respectively. However, the method 400 can be performed on other electrical components of the communication device 100 with either the first sensor assembly 122 or the second sensor assembly 126 coupled to the electrical component.

At block 402, the electronic processor 102 receives, from the first sensor assembly 122, a series of measurements corresponding to an electrical characteristic. The electrical characteristic may be a current or a voltage. For example, in the case of the first sensor assembly 122, the electrical characteristic obtained by sampling the reflected reverse voltage between the transceiver 108 and the antenna 110. In the case of the second sensor assembly 126, the electrical characteristic is the current from the battery 114 to the power circuitry 117. From the series of measurements, a first electrical characteristic profile is determined (block 404). The first electrical characteristic profile is a time series of data points of the electrical characteristic. In some embodiments, the electronic processor 102 is configured to create a history based on the series of measurements when the push-to-talk button 118 of the communication device 100 is keyed and determine the first electrical characteristic profile based on the history.

At block 406, the first electrical characteristic profile is compared to a predetermined electrical characteristic profile to generate a comparison. For example, the first electrical characteristic profile is compared to the first predetermined electrical characteristic profile 150 or the second predetermined electrical characteristic profile 151. In the example embodiment, a predetermined electrical characteristic profile is a profile of the electrical characteristic used to determine when the connector is loose. In some embodiments, the predetermined electrical characteristic profile includes a predetermined electrical characteristic pattern indicative of a loose connection within the communication device 100. The predetermined electrical characteristic pattern may be a predetermined profile, for example, based on a series of measurements made during a simulation of a loose connection within the communication device 100. The loose connection may be one or more of a loose component or cable, for example a loose battery connector 116 or loose antenna connector 112. The predetermined electrical characteristic profile may also be a predetermined ideal profile based on one or more of an ideal electrical characteristic or a series of measurements made during normal operation of the communication device 100. In alternative embodiments, the predetermined electrical characteristic profile includes predetermined electrical characteristic patterns indicative of other types of component faults, for example, a detuned antenna, a damaged battery, a faulty connector, and the like.

In some embodiments, the electronic processor 102 determines a possible loose connection when the first electrical characteristic profile differs from the predetermined electrical characteristic profile by a predetermined threshold or more. For example, if the predetermined electrical characteristic profile is based on an ideal characteristic profile, if the first electrical characteristic profile differs from the predetermined electrical characteristic profile by more than a predetermined threshold, there may be a loose connection. In some embodiments, the electronic processor 102 uses a pattern recognition process to compare the first electrical characteristic to the predetermined electrical characteristic profile. The pattern recognition process may be performed using a combination of algorithms and calculations including, for example, using a Hamming distance. The results of the pattern recognition process may be compared to a predetermined threshold to determine a possible loose connection. In some embodiments, the electronic processor 102 determines a possible loose connection when the first electrical characteristic profile matches the predetermined electrical characteristic profile within a predetermined threshold. For example, if the predetermined electrical characteristic profile is based on a simulation of a loose connection, if the first electrical characteristic profile matches the predetermined electrical characteristic profile within a predetermined threshold, there may be a loose connection.

Figure 5A:
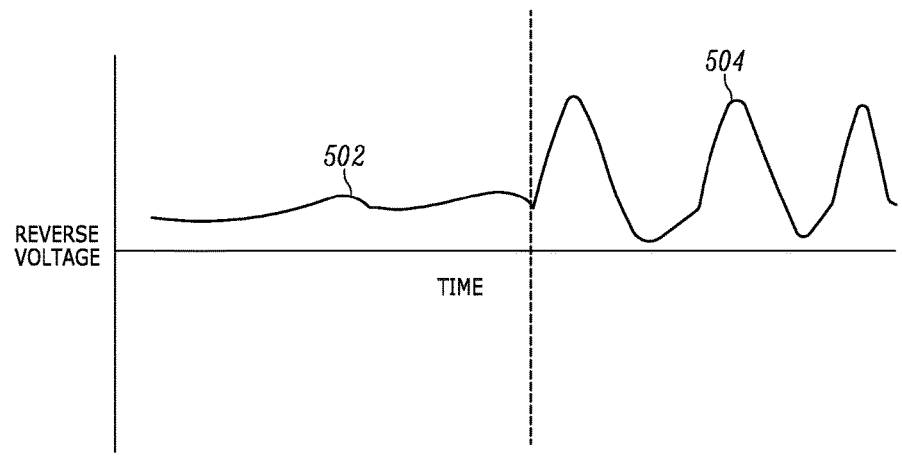
FIG. 5A illustrates an example of a first reverse voltage characteristic profile in normal operation and a predetermined electrical characteristic profile.

FIG. 5A illustrates, for the first sensor assembly 122, an example of a first reverse voltage characteristic profile 502 in normal operation (for example, when all electrical connections are complete) and a predetermined electrical characteristic (reverse voltage) profile 504. The first reverse voltage characteristic profile 502, in normal operation, does not include abrupt fluctuations (jitters), unlike in the predetermined electrical characteristic (reverse voltage) profile 504. Such fluctuations may indicate, for example, that the antenna connector 112 is loose.

Figure 5B:
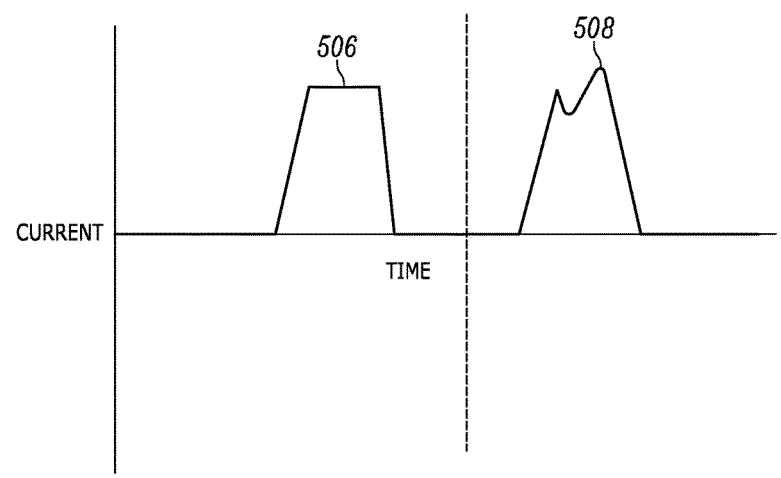
FIG. 5B illustrates an example of a first current characteristic profile in normal operation and a predetermined electrical characteristic profile.

FIG. 5B illustrates, for the second sensor assembly 126, an example of a first current characteristic profile 506 in normal operation and a predetermined electrical characteristic (current) profile 508. The first current characteristic profile 506, in normal operation, does not include fluctuations, unlike in the predetermined electrical characteristic (current) profile 508. Such fluctuations may indicate the battery connector 116 is loose.

Returning to FIG. 4, at block 408, the electronic processor 102 generates an indication of a possible component fault (for example, a loose connection) based on the comparison between the first electrical characteristic and the predetermined electrical characteristic. In some embodiments, the electronic processor 102 may generate the indication based on a result of the pattern recognition process. In further embodiments, when the electronic processor 102 determines, based on the comparison, that there is a loose connection, the electronic processor 102 executes the method 400 at block 406 and compares the first electrical characteristic profile to a different predetermined electrical characteristic profile to determine the location of the loose connection/component.

For example, the first predetermined electrical characteristic profile 150 is based on ideal electrical characteristics and the second predetermined electrical characteristic profile 151 is based on a series of measurements made during a simulation of a loose connection within the communication device 100. From the comparison between the first electrical characteristic profile 150 and the first predetermined electrical characteristic profile 150, the electronic processor 102 determines there is a loose connection and generates an indication of that loose connection. The electronic processor 102 then compares the first electrical characteristic profile to the second predetermined electrical characteristic profile 151 to determine the location of the loose connection. When the first electrical characteristic profile matches the second predetermined electrical characteristic profile 151, then the location associated with the second predetermined electrical characteristic profile 151 is determined to be the location of the possible loose connection.

In one example, when the first electrical characteristic profile 150 does not match the second predetermined electrical characteristic profile 151, the first electrical characteristic profile 150 is compared to a plurality of predetermined electrical characteristic profiles to determine the location of the possible loose connection.

The subsequent predetermined electrical characteristic profiles that the first electrical characteristic profile is compared to may each include a profile based on a series of measurements made during a simulation of one or more different loose connections within the communication device 100. Thus, the location of the loose connection and/or loose component within the communication device 100 may be identified by comparing multiple different predetermined electrical characteristic profiles to the first electrical characteristic profile 150. When the electronic processor 102 determines there is no loose connection, the electronic processor 102 repeats the method 400 and returns to block 402.

The indication may be presented by a visual signal for presentation on the display 120, an audio signal, or an error signal for recordation in a log in the communication device 100. In some embodiments, the electronic processor 102 is further configured to send the error signal to an error log stored in either a local memory, for example the memory 104, or a remote server or database. The indication may also include the location of the loose connection and/or loose component based on the comparison between the first electrical characteristic profile and the predetermined electrical characteristic profile.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms for example first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") for example microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

I claim:

1. A communication device comprising:
an electrical component;
a sensor coupled to the electrical component and configured to sense an electrical characteristic of the electrical component; and
an electronic processor connected to the sensor and configured to:
receive, from the sensor, a series of measurements corresponding to the electrical characteristic;
determine, from the series of measurements, a first electrical characteristic profile;
compare the first electrical characteristic profile to a predetermined electrical characteristic profile to generate a comparison;
generate an indication of a possible component fault based on the comparison; and
compare the first electrical characteristic profile to a plurality of predetermined electrical characteristic profiles to determine a location of the possible component fault.

2. The communication device of claim 1, wherein the predetermined electrical characteristic profile is based on at least one selected from the group consisting of a predetermined ideal profile based on one or more ideal electrical characteristics, a series of measurements made during normal operation of the communication device, a predetermined electrical characteristic pattern indicative of a component fault within the communication device, and a series of measurements made during a simulation of a component fault within the communication device.

3. The communication device of claim 1, wherein the electrical characteristic is a current or a voltage.

4. The communication device of claim 1, further comprising an antenna and wherein the electrical component is a transmitter coupled to the antenna via a transmission line.

5. The communication device of claim 1, wherein the electronic processor is further configured to receive, from the sensor, the series of measurements corresponding to the electrical characteristic by sampling a reverse voltage.

6. The communication device of claim 1, wherein the electronic processor compares the first electrical characteristic profile to the predetermined electrical characteristic profile using a pattern recognition process and generates the indication based on a result of the pattern recognition process.

7. The communication device of claim 6, wherein the pattern recognition process includes determining a Hamming distance.

8. The communication device of claim 1, wherein the indication of the possible component fault is at least one selected from a group consisting of a visual signal for presentation on a display, an audio signal, and an error signal for recordation in a log in the communication device.

9. The communication device of claim 1, wherein the indication is an error signal and the electronic processor is further configured to send the error signal to an error log.

10. The communication device of claim 1, wherein the electronic processor is further configured to receive, from the sensor, the series of measurements corresponding to the electrical characteristic by sampling a current from a power amplifier current sensor.

11. The communication device of claim 1, wherein the electronic processor is further configured to:
create a history based on the series of measurements when a button of the communication device is keyed; and
determine the first electrical characteristic profile based on the history.

12. A method for operating a communication device, the method comprising:
receiving, from a sensor, a series of measurements corresponding to an electrical characteristic;
determining, from the series of measurements, a first electrical characteristic profile;
comparing the first electrical characteristic profile to a predetermined electrical characteristic profile, generating a comparison;
generating an indication of a possible component fault based on the comparison; and
comparing the first electrical characteristic profile to a plurality of predetermined electrical characteristic profiles to determine a location of the possible component fault.

13. The method of claim 12, wherein the predetermined electrical characteristic profile is based on at least one selected from the group consisting of a predetermined ideal profile based on one or more ideal electrical characteristics, a series of measurements made during normal operation of the communication device, a predetermined electrical characteristic pattern indicative of a component fault within the communication device, and a third series of measurements made during a simulation of a component fault within the communication device.

14. The method of claim 12, wherein the electrical characteristic is a current or a voltage.

15. The method of claim 12, wherein the series of measurements corresponding to the electrical characteristic is obtained by sampling a reverse voltage or a current from a power amplifier current sensor.

16. The method of claim 12, further comprising comparing the first electrical characteristic profile to the predetermined electrical characteristic profile using a pattern recognition process and generating the indication based on a result of the pattern recognition process.

17. The method of claim 12 further comprising:
creating a history based on the series of measurements when a button of the communication device is keyed; and
determining the first electrical characteristic profile based on the history.

18. A portable radio communication device comprising:
an antenna;
a transmitter coupled to the antenna via a transmission line;
a sensor coupled to the transmission line and configured to sense an electrical characteristic of the transmission line;
an electronic processor connected to the sensor and configured to:
receive, from the sensor, a series of measurements corresponding to the electrical characteristic;
determine, from the series of measurements, a first electrical characteristic profile;

compare the first electrical characteristic profile to a predetermined electrical characteristic profile to generate a comparison;
generate an indication of a possible component fault based on the comparison; and
compare the first electrical characteristic profile to a plurality of predetermined electrical characteristic profiles to determine a location of the possible component fault.

19. A communication device comprising:
an electrical component;
a sensor coupled to the electrical component and configured to sense an electrical characteristic of the electrical component; and
an electronic processor connected to the sensor and configured to:
  receive, from the sensor, a series of measurements corresponding to the electrical characteristic;
  determine, from the series of measurements, a first electrical characteristic profile;
  compare the first electrical characteristic profile to a predetermined electrical characteristic profile to generate a comparison;
  generate an indication of a possible component fault based on the comparison; and
an antenna and wherein the electrical component is a transmitter coupled to the antenna via a transmission line.

20. A communication device comprising:
an electrical component;
a sensor coupled to the electrical component and configured to sense an electrical characteristic of the electrical component; and
an electronic processor connected to the sensor and configured to:
  receive, from the sensor, a series of measurements corresponding to the electrical characteristic;
  determine, from the series of measurements, a first electrical characteristic profile;
  compare the first electrical characteristic profile to a predetermined electrical characteristic profile to generate a comparison;
  generate an indication of a possible component fault based on the comparison; and
  wherein the electronic processor is further configured to receive, from the sensor, the series of measurements corresponding to the electrical characteristic by sampling a reverse voltage or sampling a current from a power amplifier current sensor.

21. A communication device comprising:
an electrical component;
a sensor coupled to the electrical component and configured to sense an electrical characteristic of the electrical component; and
an electronic processor connected to the sensor and configured to:
  receive, from the sensor, a series of measurements corresponding to the electrical characteristic;
  determine, from the series of measurements, a first electrical characteristic profile;
  compare the first electrical characteristic profile to a predetermined electrical characteristic profile to generate a comparison;
  generate an indication of a possible component fault based on the comparison;
  create a history based on the series of measurements when a button of the communication device is keyed; and
  determine the first electrical characteristic profile based on the history.

22. A method for operating a communication device, the method comprising:
receiving, from a sensor, a series of measurements corresponding to an electrical characteristic;
determining, from the series of measurements, a first electrical characteristic profile;
comparing the first electrical characteristic profile to a predetermined electrical characteristic profile, generating a comparison;
generating an indication of a possible component fault based on the comparison; and wherein the series of measurements corresponding to the electrical characteristic is obtained by sampling a reverse voltage or a current from a power amplifier current sensor.

23. A method for operating a communication device, the method comprising:
receiving, from a sensor, a series of measurements corresponding to an electrical characteristic;
determining, from the series of measurements, a first electrical characteristic profile;
comparing the first electrical characteristic profile to a predetermined electrical characteristic profile, generating a comparison;
generating an indication of a possible component fault based on the comparison;
creating a history based on the series of measurements when a button of the communication device is keyed; and
determining the first electrical characteristic profile based on the history.

\* \* \* \* \*